United States Patent [19]

Sabal

[11] Patent Number: 5,610,071
[45] Date of Patent: Mar. 11, 1997

[54] METHOD OF HAIR ANALYSIS

[76] Inventor: Jacqueline A. Sabal, 315 SE. Mizner Blvd. Ste. 204, Boca Raton, Fla. 33432

[21] Appl. No.: 549,484

[22] Filed: Oct. 27, 1995

Related U.S. Application Data

[63] Continuation-in-part of Ser. No. 228,680, Apr. 18, 1994, abandoned.
[51] Int. Cl.$^6$ .............................. G01N 1/00; G01N 33/48
[52] U.S. Cl. ................................ 436/79; 436/80; 436/81; 436/83; 436/84; 436/174
[58] Field of Search .................................. 436/63, 73, 74, 436/77, 79, 80, 81, 83, 84, 171, 174, 175; 435/29; 424/9.1, 9.2, 9.8, 70.1

[56] References Cited

U.S. PATENT DOCUMENTS 3,910,284 10/1975 Orentreich .
4,946,678 8/1990 Dodd et al. .
5,228,431 7/1993 Giarretto .

OTHER PUBLICATIONS

FDC Reports: The Rose Sheet, vol. 12, issue 35, Sep. 2, 1991 – See Abstract.
Friel et al., Clinical Chemistry, vol. 32/5, pp. 739–742, 1986.
Pomeroy et al., Journal of Chemical Education, vol. 52, No. 8, Aug. 1975, pp. 544–545.
Aharoni et al., American Journal of Clinical Nutrition, vol. 55, 1992, pp. 104–107.
Okamoto et al., Clinical Chemistry, vol. 31/10, pp. 1592–1597, 1985.

*Primary Examiner*—Jeffrey Snay

[57] ABSTRACT

A method of hair analysis that provides an extensive history is disclosed. The method includes the steps of: (1) releasing trapped hair from a hair follicle; and, (2) performing hair analysis on the released hair.

4 Claims, 3 Drawing Sheets

METHOD OF HAIR ANALYSIS

This is a continuation-in-part of U.S. Ser. No. 08/228,680, filed Apr. 18, 1994, now abandoned.

FIELD OF THE INVENTION

This invention relates generally to hair analysis and, in particular, to an improved method of hair analysis that provides an extensive history.

BACKGROUND OF THE INVENTION

Hair analysis has become an exciting subject of scientific inquiry. In the past, the value of assessing the nutritional status of patients with respect to essential metals has not been appreciated. It is only recently that research findings are being correlated and applied to the diagnosis of sub-clinical and chronic disease.

Hair is known to retain metals. Hair analysis has been used extensively to detect toxic concentrations of heavy metals such as arsenic, chromium, lead, mercury, and cadmium. Its use to detect essential metals such as zinc and copper is less well known.

Through hair analysis, we are now learning more about how mineral deficiencies affect the composition of body tissue. Ingested minerals are assimilated by different people at different rates and are needed in different proportions by different tissues. Hair analysis affords a graphic record of the intracellular reactions and interactions of the enzymes activated by metals during a period of three to four weeks preceeding the sampling.

Most sub-clinical and chronic diseases manifest themselves over periods of longer than three to four weeks. Accordingly, it would be desirable to analyze hair that has been growing for a longer period of time.

It is, therefore, an object of the invention to provide an improved method of hair analysis that provides an extensive history.

It is another object of the invention to provide a method of hair analysis that can be used to diagnose sub-clinical and chronic disease over an extended period of time.

Other objects and advantages of the invention will in part be obvious and will in part be apparent from the specification.

SUMMARY OF THE INVENTION

Generally speaking, applicant's invention is an improved method of hair analysis that provides an extensive history. The method includes the steps of: (1) releasing trapped hair from a hair follicle; and, (2) performing hair analysis on the released hair.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

The method of hair analysis provided in accordance with the invention includes releasing entrapped hair from a hair follicle to provide released hair and performing hair analysis on the released hair. This method provides a more extensive history of metal absorption than has heretofore been possible.

Although an individual hair is dead, a head of hair is a living, growing thing. A cross sectional view of a hair follicle 14 with a growing hair 10 therein is shown in FIG. 1.

Figure 1:
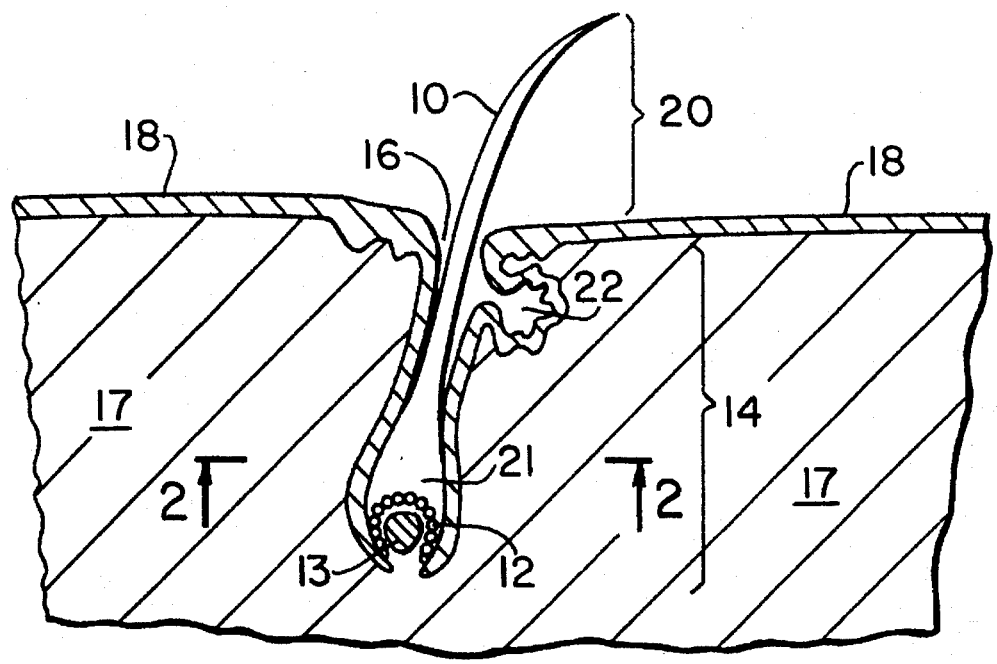
FIG. 1 is a cross-sectional view of a normal hair follicle with growing hair.

As shown in FIG. 1, a hair 10 originates in germinative cells 12 and papilla 13 and extends through the hair follicle 14, a tube-like pocket in the skin 17. The follicle 14 directs the hair 10 to the skin surface 18. When the hair 10 passes an opening 16 through the skin surface 18, the hair can be observed visually. The portion of the hair 10 that projects from the skin surface 18 is called a hair shaft 20. The portion of the hair 10 that lies within the skin 17 below the skin surface 18 is a root 21.

There are about 2,000 hair follicles 14 per square inch of skin 17 covering the top of a human head, i.e. the scalp. Each follicle 14 has attached oil or sebaceous glands 22 and adjacent sweat glands.

The period of active growth of each hair 10, known as anagen, lasts from about 18 months to several years. Usually hair grows at a rate of about one half inch per month, Hair growth slows, however, as the hair gets longer or if the person is ill. Growth is also affected by seasons and is generally faster in summer and slower in winter.

Figure 2:
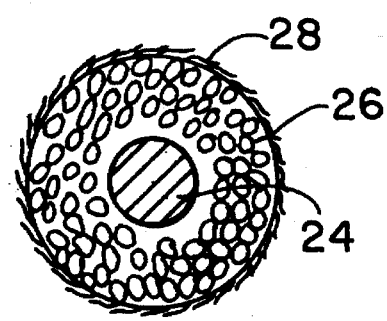
FIG. 2 is a cross-sectional view of a single hair taken through section line 2—2 of FIG. 1.

Hair is composed of protein or keratin, a filament-like outgrowth on the skin. A cross-section of a single hair is shown in FIG. 2. The hair has a center or medula 24, a layer of spindle cells or cortex 26 and several layers of cuticle cells 28, which resemble fish scales. The spindle cells 26 contain pigment or melanin that gives hair its characteristic colors. These spindle cells 26 are easily rearranged by application of various chemicals or heat.

The hair root 21 is nourished directly by the blood supply. Many factors in the blood supply are affected by diet and, in particular, by vitamins, minerals and protein supplements entering the body. As a consequence, the composition and appearance of the hair 10 is affected by the diet ingested.

In a second stage, known as catagen, hair growth stops, but the hair 10 remains in place in the follicle 14. Finally, the hair 10 falls out of the follicle 14 and a new hair begins to grow in its place. This final stage is known as telogen.

Figure 3:
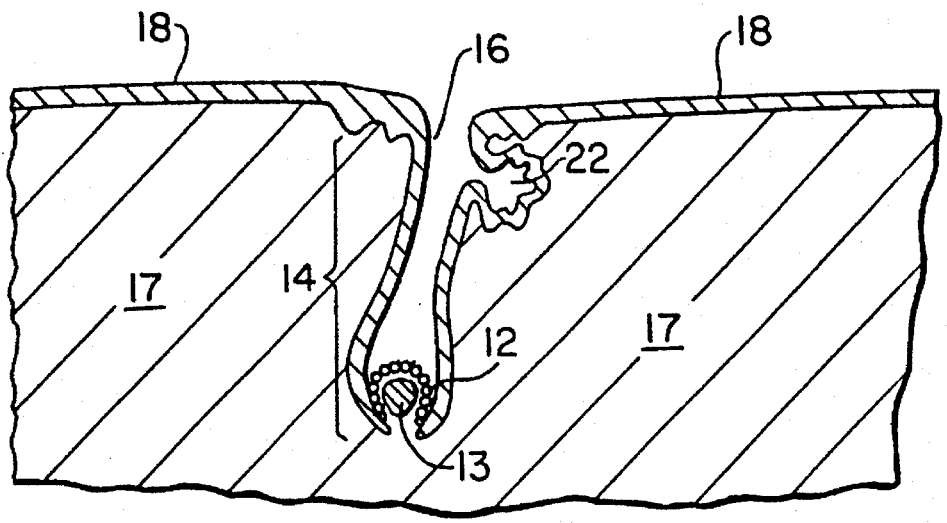
FIG. 3 is a cross-sectional view of a normal hair follicle in a resting state.

Every day between about 50 and 150 hairs fall out of a normal scalp in preparation for replacement by new hair. A cross-sectional view of a hair follicle in this resting state, i.e. telogen, is shown in FIG. 3. Oil produced by the sebaceous glands 22 along with other debris may accumulate at the opening 16 of the follicle 14 when the hair follicle is open.

Figure 4:
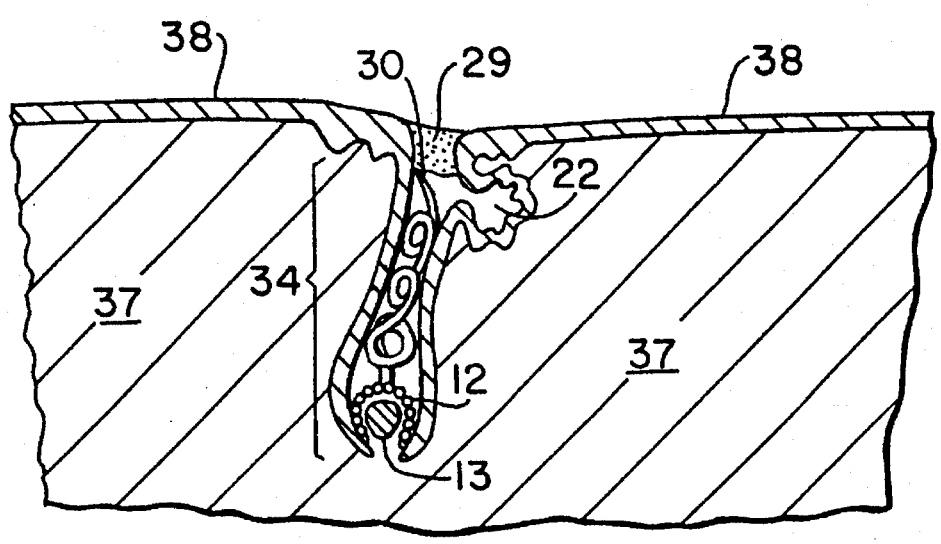
FIG. 4 is a cross-sectional view of a hair follicle having entrapped hair.

It is believed that the oil and other accumulated debris can be an important contributing cause of hair loss and baldness on the scalp. Excess fluid produced by overproducing glands 22 in combination with airborne pollutants create a substance that cannot be dissolved by regular shampoos. This substance forms a plug 29 that blocks a hair follicle 34 so that there is no opening through skin 37. Accordingly, hairs 30 growing within the follicles 34 are trapped as shown in FIG. 4.

It has been postulated that hair is constantly growing even on bald scalps, i.e., the bald appearance of certain scalps is not due to the failure of the hair follicles to grow hair, but to the failure of the hair 30 to penetrate an opening through the skin surface 38. As a result, the scalp gradually takes on a bald appearance. This has, in fact, been confirmed in some cases by examining the scalps of cadavers.

It is possible to release entrapped hair 30 from the hair follicles 34 found on so-called bald scalps. This can be done, for example, using Foli-Kleen 2000™, a product of Sable Laboratories, Inc., Pompano Beach, Florida. Foli-Kleen 2000™ is an herbal formulation that gently cleans away the oil and debris accumulated in the hair follicle. Specifically, Foli-Kleen 2000™ herbal formulation deep cleanses the scalp, dissolves oil, and carries away surface dirt, dandruff and other follicle clogging agents. This creates an environment in which hair can thrive, resulting in thick, full and healthy looking hair.

Foli-Kleen 2000™ herbal formulation is available in two formulations, which are identified as Formula I and Formula II. Foli-Kleen 2000™ herbal formulation Formulas I and II create a dual action cleansing activity that enhances the look and feel of the hair and should be used in conjunction with one another for maximum results.

Foli-Kleen 2000™ Formula I is a first herbal formulation including water, sodium cocoate, sulfonated castor oil, lanolin, Germaben 2, chamomile, lecithin, kelp, burdock, and mixed herbal fragrances. Foli-Kleen 2000™ Formula II is a second herbal formulation including witch hazel, alcohol, lanolin, Germaben 2, cohash extract, kelp, burdock, and mixed herbal fragrances.

To use Foli-Kleen 2000™ herbal formulation, a small amount of Formula I is applied to a dry scalp and left on the scalp for a short period of time to allow the scalp to absorb the Foli-Kleen 2000™ Formula I. A second small amount of Formula I is applied and left on the scalp for a second short period of time. Then the Formula I is completely rinsed with water to remove loosened debris and the scalp is dried.

A generous amount of Formula II is applied to the dried scalp, preferably using a soft brush. The scalp is brushed in a back and forth motion of about one inch. Formula II is blow dried onto the scalp and allowed to remain for a period of between about 12 and 24 hours. Then Formula I is applied again and the process is repeated. A noticeable difference in the amount of visible hair is generally observed within a few months and the process is generally completed within about one year.

Figure 5:
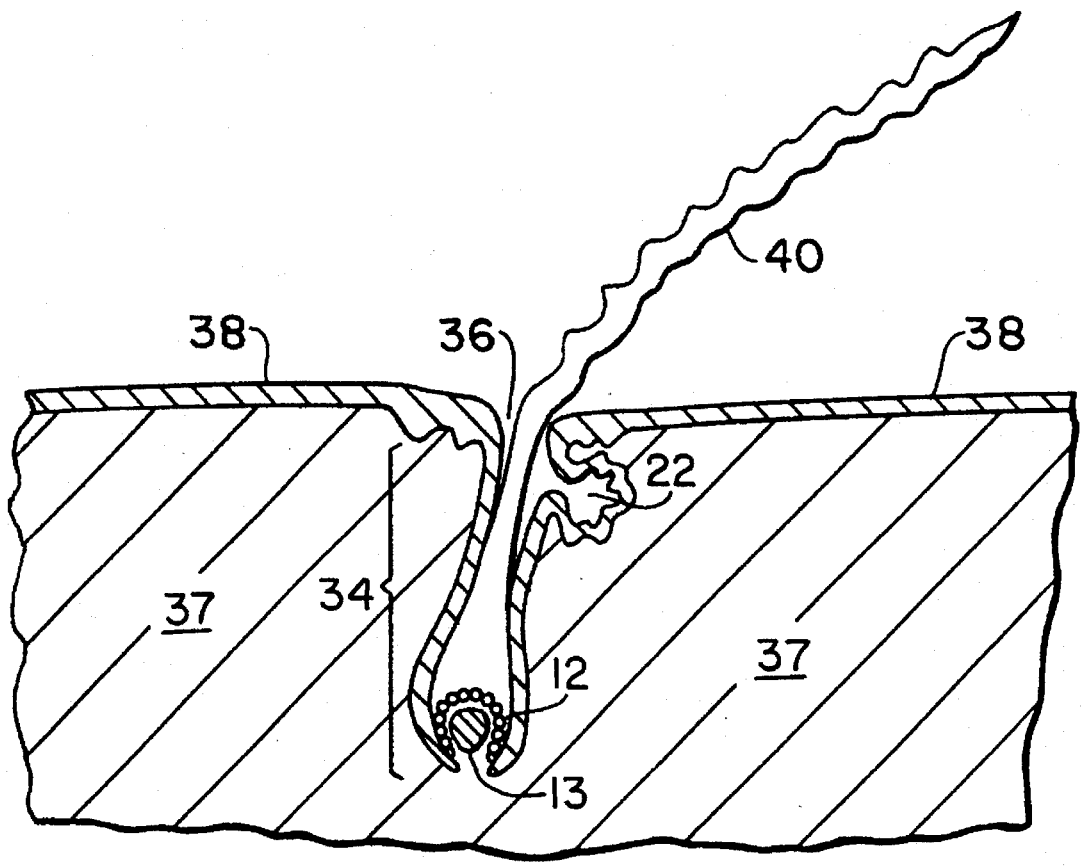
FIG. 5 is a cross-sectional view of a hair follicle wherein entrapped hair has been released.

As described, Foli-Klenn 2000™ herbal formulation gently cleans debris clogging the hair follicle 34. Accordingly, hair 30 trapped in the follicle 34 is released and extends through a new opening 36 through the skin surface 38 as shown in FIG. 5. A new hair shaft 40 is created thereby. The hair shaft is generally long and kinky-curly due to its extended period of entrapment in the hair follicle 34. Although some results can be observed immediately, continued use of the Foli-Kleen 2000™ herbal formulas over a period of 30 to 60 days may be required before significant results are observed. In general, treatment can be completed within one year.

The released hair shaft 40 is useful for performing hair analysis due to its extended period of entrapment in the hair follicle 34. Prior to the method provided in accordance with the invention, hair analysis was, and still is, performed on hair clipped from the back of the neck, close to the scalp.

Hair that grows close to the skin is preferred due to the fact that spindle cells 26 can be rearranged or changed due to the use of shampoos, other hair preparations, or exposure to the elements. Accordingly, inaccurate readings can be obtained by using hair that has been growing for any length of time as determined by its distance from the skin surface.

To perform hair analysis, the hair specimen is thoroughly washed and digested to a liquid. The residue is analyzed for mineral content by atomic absorption spectroscopy. Hair analysis reveals levels of minerals in the body, ratios, and health trends.

Minerals are essential to many body functions and are vital to a person's overall mental and physical well-being. Many nutritional minerals are believed to be beneficial and necessary for life. These minerals include, for example, calcium, sodium, iron, manganese, chromium, molybdenum, phosphorus, cobalt, vanadium, magnesium, potassium, copper, zinc, selenium, nickel, lithium, and tin.

As examples of the roles played by certain minerals, a low zinc level may be indicative of problems with wound healing, growth and sexual maturation since zinc is an activator of carbonic anhydrase and is required for mobilization of vitamin A from the liver. Low manganese level s are observed in some chondrodystrophies and other connective tissue disorders. Finally, a low tin level may inhibit adequate growth and development since tin is believed to function in oxidation-reduction reactions used in the production of energy.

High mineral levels can also be a problem. For example, a high phosporous level may indicate a problem with calcium and vitamin D intake since calcium and vitamin D are believed to play a role in proper phosporous utilization. A high sodium level may indicate a predisposition to congestion and edema.

At extremely elevated levels, almost any mineral will exhibit some signs of toxicity. However, certain minerals including, for example, lead, mercury, arsenic, cadmium, and aluminum exhibit adverse metabolic effects at extremely low concentrations of a few parts per million.

For example, lead accumulation is a problem because it is associated with hyperactivity and nervous disorders. Lead is believed to interfere with a variety of enzymatic activities. It has an affinity for bone and may create an unstable bone matrix.

Finally, the ratios of certain minerals are as important as the precise amount of each that is present. For example, calcium utilization is affected by decreased levels of sodium, potassium, manganese, and by increased levels of magnesium. Manganese is necessary, for example, for calcium stability in the bone matrix.

Hair analysis by atomic absorption spectroscopy can be used to detect the presence, amount, and relative ratios of all of the minerals discussed. It is more effective than blood or urine sampling in some instances since it provides a record of what is being stored in the body.

It can readily be seen that by performing hair analysis on a released hair shaft 40 a more accurate and extensive history of mineral absorption in the body due to the long period of growth of the hair shaft 40 in the hair follicle 34 prior to its release. Such an extensive history had not previously been available. Hair that has been growing an equivalent length of time that has not been entrapped in a hair follicle can be affected by certain shampoos and other hair preparations and accordingly, the results may not be as accurate.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method of hair analysis to determine a history of mineral absorption comprising:

releasing a trapped grown hair from a clogged hair follicle;

removing said released hair from said follicle; and determining mineral absorption in said removed hair by atomic absorption spectroscopy analysis;

wherein said step of releasing comprises contacting said dogged follicle with a formulation in a manner and amount effective for unclogging said clogged follicle, whereby said trapped hair is released and extended through said unclogged follicle; and further wherein said contacting step comprises applying to a scalp containing said clogged follicle a first herbal formulation for a first period of time sufficient to enable the first formulation to be absorbed into the scalp, rinsing the first formulation from the scalp, and applying a second herbal formulation to the scalp for a second period of time sufficient to enable said clogged follicle to become unclogged.

2. The method of claim 1 wherein said contacting step is repeated daily until a plurality of said trapped hairs are released.

3. The method of claim 1 wherein the removed hair is washed and digested prior to performing said spectroscopy analysis.

4. The method of claim 1 wherein said detecting step comprises measuring the presence and amount of at least one mineral selected from the group consisting of calcium, sodium, iron, manganese, chromium, molybdenum, phosphorus, cobalt, vanadium, magnesium, potassium, copper, zinc, selenium, nickel, lithium, tin, lead, mercury, arsenic, cadmium, aluminum, and combinations thereof.

* * * * *